United States Patent
Irrgang et al.

(10) Patent No.: US 11,931,494 B2
(45) Date of Patent: Mar. 19, 2024

(54) DIALYSIS MACHINE FOR CARRYING OUT A PUSH/PULL DIALYSIS TREATMENT

(71) Applicant: FRESENIUS MEDICAL CARE DEUTSCHLAND GMBH, Bad Homburg (DE)

(72) Inventors: Tobias Irrgang, Aubstadt (DE); Benedict Glaser, Schweinfurt (DE); Peter Klöffel, Nüdlingen (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 0 days.

(21) Appl. No.: 17/775,326

(22) PCT Filed: Nov. 10, 2020

(86) PCT No.: PCT/EP2020/081654
§ 371 (c)(1),
(2) Date: May 9, 2022

(87) PCT Pub. No.: WO2021/094317
PCT Pub. Date: May 20, 2021

(65) Prior Publication Data
US 2022/0387683 A1    Dec. 8, 2022

(30) Foreign Application Priority Data
Nov. 11, 2019   (DE) ............... 10 2019 130 294.3

(51) Int. Cl.
*A61M 1/16*    (2006.01)
*A61M 1/34*    (2006.01)

(52) U.S. Cl.
CPC ........ *A61M 1/1639* (2014.02); *A61M 1/1694* (2013.01); *A61M 1/3413* (2013.01); *A61M 1/3427* (2014.02); *A61M 1/3465* (2014.02)

(58) Field of Classification Search
None
See application file for complete search history.

(56) References Cited

U.S. PATENT DOCUMENTS

| | | | |
|---|---|---|---|
| 4,079,007 A * | 3/1978 | Hutchisson | A61M 1/1605 210/321.71 |
| 4,997,570 A | 3/1991 | Polaschegg | |

(Continued)

FOREIGN PATENT DOCUMENTS

| | | | |
|---|---|---|---|
| DE | 38 37 498 A1 | 5/1990 | |
| DE | 3736712 C2 * | 3/1995 | A61M 1/16 |

(Continued)

*Primary Examiner* — Krishnan S Menon
(74) *Attorney, Agent, or Firm* — Jacobson Holman PLLC

(57) ABSTRACT

The invention relates to a dialysis machine having a fluid system that has an inflow line for providing fresh dialyzing solution to a dialyzer and an outflow line for removing used dialyzing solution from the dialyzer, wherein the fluid system has a balancing system arranged between the inflow and outflow lines to balance the fluid volumes flowing through the lines, and wherein the fluid system has an ultrafiltration line that branches off from the outflow line between the dialyzer and the balancing system and has an ultrafiltration pump to be able to remove a defined volume of used dialyzing solution from the balance, and wherein an additional balancing chamber is provided that is arranged in a section of the inflow line disposed between the balancing system and the dialyzer or in a section of the outflow line disposed between the dialyzer and the branching of the ultrafiltration line.

15 Claims, 9 Drawing Sheets

(56) References Cited

U.S. PATENT DOCUMENTS

Figure 1:
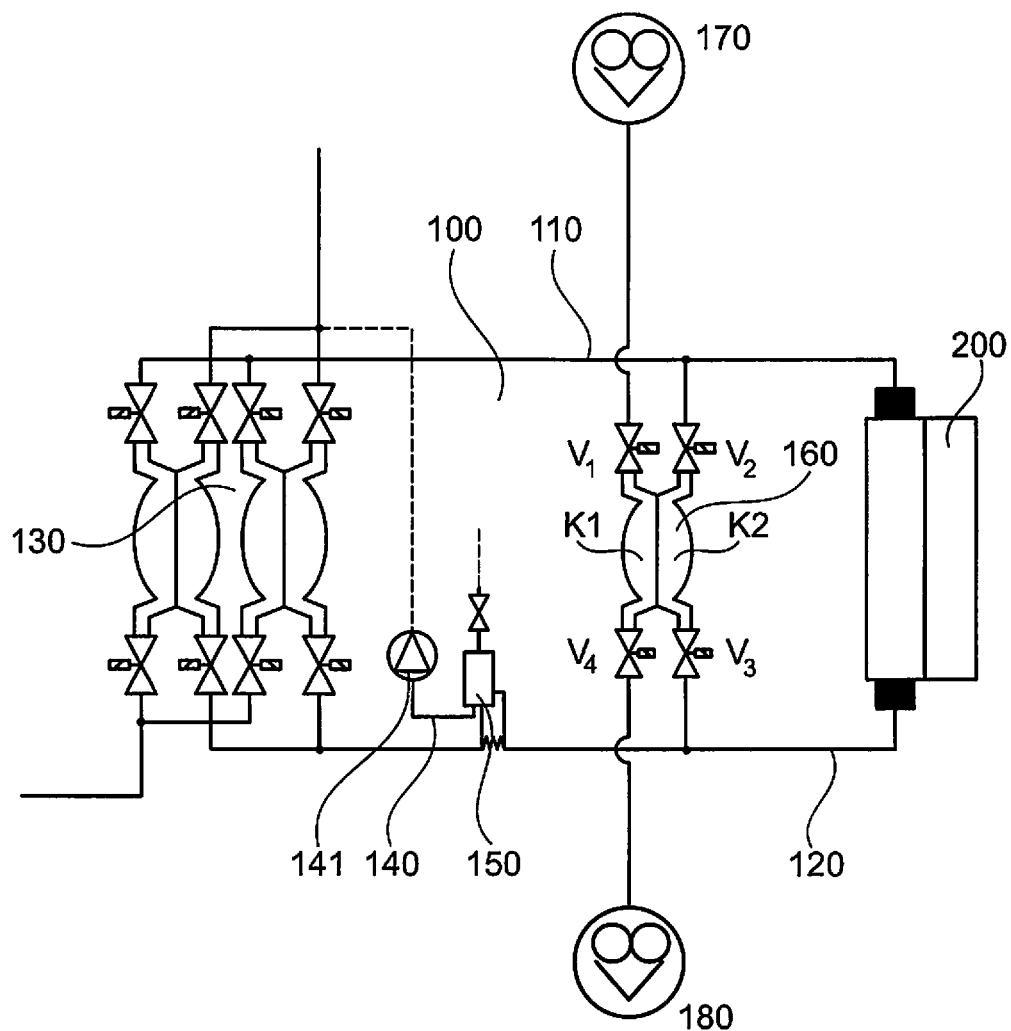

| | | | | |
|---|---|---|---|---|
| 6,042,784 A | * | 3/2000 | Wamsiedler | ........ A61M 1/1639 |
| | | | | 604/4.01 |
| 2009/0008306 A1 | | 1/2009 | Cicchello et al. | |
| 2012/0316799 A1 | | 12/2012 | Gagel | |
| 2013/0087210 A1 | * | 4/2013 | Brandl | ................ A61M 1/1694 |
| | | | | 137/115.01 |

FOREIGN PATENT DOCUMENTS

| | | |
|---|---|---|
| DE | 197 08 391 C1 | 10/1998 |
| DE | 198 30 928 C1 | 5/1999 |
| DE | 10 2014 109639 A1 | 1/2016 |
| EP | 0867195 A1 | 9/1988 |

* cited by examiner

DIALYSIS MACHINE FOR CARRYING OUT A PUSH/PULL DIALYSIS TREATMENT

The invention relates to a dialysis machine for carrying out a push/pull dialysis treatment.

In hemodialysis or hemodiafiltration, the dialyzer is flowed through by blood and dialyzing solution in opposite directions. Due to the counterflow principle, the blood pressure relative to the dialyzing solution is greater at the blood input side of the dialyzer than at the blood output side of the dialyzer. With a typical process management, the transmembrane pressure is therefore positive in the blood input region (the proximal region) of the dialyzer, which results in a net fluid transfer in the direction of the dialyzate chamber of the dialyzer and in so-called forward filtration in this region, and is negative in the blood output region (the distal region) of the dialyzer, which results in a net fluid transfer in the direction of the blood chamber of the dialyzer and in so-called backward filtration in this region. The backward filtration admittedly produces a fluid balance and can be used to set the fluid loss, but it reduces the efficiency of the dialysis overall.

Forward filtration over the total length of the dialyzer can be achieved by a lowering of the dialysis fluid pressure relative to the blood pressure in a similar manner to backward filtration over the total length of the dialyzer by a raising of the dialysis fluid pressure relative to the blood pressure. So-called push/pull processes utilize this circumstance to alternatingly achieve forward filtration and backward filtration by pressure variation over the total length of the dialyzer. This can produce an increase in efficiency overall on the removal of uremic toxins from the blood. An overview of the known options for implementing push/pull processes is provided by the review article Kyongsoo Lee (2013) Engineering perspective on the evolution of push/pull-based dialysis treatments, Expert Review of Medical Devices, 10:5, 611-620.

It is the object of the invention to provide a dialysis machine having the ability to provide a push/pull dialysis treatment that is advantageous in comparison with known solutions.

Against this background, the invention relates to a dialysis machine having a fluid system that has an inflow line for providing fresh dialyzing solution to a dialyzer and an outflow line for removing used dialyzing solution from the dialyzer, wherein the fluid system has a balancing system arranged between the inflow and outflow lines to balance the fluid volumes flowing through the lines, and wherein the fluid system has an ultrafiltration line that branches off from the outflow line between the dialyzer and the balancing system and has an ultrafiltration pump to be able to remove a defined volume of used dialyzing solution from the balance.

In accordance with the invention, an additional balancing chamber is provided that is arranged in a section of the inflow line disposed between the balancing system and the dialyzer or in a section of the outflow line disposed between the dialyzer and the branching of the ultrafiltration line.

One of the chambers of the balancing chamber connects the section of the inflow line disposed between the balancing system and the dialyzer to the section of the outflow line disposed between the dialyzer and the branching of the ultrafiltration line.

The additional balancing chamber is not a balancing chamber in the true sense since it does not satisfy any balancing function. It is, however, a balancing chamber according to its design so that this term will be used in the present description. The additional balancing chamber arranged close to the dialyzer enables a push/pull operation during the dialysis treatment without additional construction measures being required at the dialysis machine.

Provision can in particular be made that the additional balancing chamber has a container of preferably fixed volume that is divided into two chambers by a preferably elastic membrane, wherein a connector for connecting the first chamber to the inflow is provided at a first one of the chambers and a connector for connecting the first chamber to the outflow line is provided, and wherein a valve for opening and closing the respective connector is arranged at both connectors.

Provision is further preferably made that at least one connector is provided at the other one of the chambers, that is the second chamber, for connecting the second chamber to a fluid control pump by which the pressure in the second chamber can be raised or lowered, wherein the connector preferably has a valve for its opening and closing. The fluid control pump can be configured here such that it can convey fluids in two directions. Alternatively, two connectors can be provided at the second chamber for connecting the second chamber to a respective fluid control pump, wherein the pressure in the second chamber can be raised or lowered by the fluid control pumps. In this case, one of the fluid control pumps is preferably configured such that it can convey fluids into the second chamber and the other one of the fluid control pumps is preferably configured such that it can remove fluids from the second chamber.

The at least one fluid control pump is provided to convey fluid into the second chamber of the additional balancing chamber or to remove fluid from this chamber. The fluid used is here preferably moved to and fro in alternating operation. It thus serves the movement of the membrane of the additional balancing chamber so that dialysis fluid can be conveyed in push/pull operation in the dialyzer in the first chamber.

Provision can furthermore be made to provide the connector or connectors of the second chamber to valves for opening and closing the respective connector. This enables a particularly precise control of the push/pull procedure.

The valves can, for example, be electrically controllable 2/2 way magnetic valves by means of which the connectors can be selectively completely opened or closed.

In a preferred embodiment, the dialysis machine has a control unit that is in signal connection with the valves of the additional balancing chamber and of the fluid control pump or pumps and that is configured to control the valves and pumps such that the pressure of the dialysis solution in the dialyzer is periodically raised and lowered by an alternating filling and emptying of the one chamber of the additional balancing chamber with/of dialyzing solution from the inflow and outflow lines.

The control unit can in particular be configured to open the valve connecting the first chamber to the inflow line in a treatment break, to close the valve connecting the first chamber to the outflow line, and to activate the fluid control pump(s) for a pressure increase in the second chamber to increase the input pressure of the dialyzing solution at the dialyzer. The fluid pressure of the dialyzing solution in the dialyzer is increased overall by increasing the input pressure with an unchanging output pressure, which increases the portion of backward filtration in the dialyzer. The control unit can accordingly in particular be configured to open the valve connecting the first chamber to the outflow line in a treatment break, to close the valve connecting the first chamber to the inflow line, and to activate the fluid control pump(s) for a pressure reduction in the second chamber to decrease the output pressure of the dialyzing solution at the dialyzer. The fluid pressure of the dialyzing solution in the dialyzer is decreased overall by decreasing the output pressure with an unchanging input pressure, which increases the portion of forward filtration in the dialyzer.

The described treatment phases to increase the input pressure or to reduce the output pressure are preferably selected alternatingly by the control unit, with selectively either a break taking place or with the transition being able to be direct between the treatment phases.

In an embodiment, the fluid system has an air separator arranged between the dialyzer and the balancing system in the outflow line and the additional balancing chamber is arranged in the section of the inflow line disposed between the balancing system and the dialyzer and the section of the outflow line disposed between the dialyzer and the air separator. The air separator can, for example, be arranged at or in the region of the branching of the ultrafiltration line at the outflow line.

The balancing device of the dialysis machine can be a balancing chamber system having two balancing chambers. The machine or more precisely its fluid system therefore comprises at least three balancing chambers in this embodiment, of which two balancing chambers actually represent part of a balancing system while the additional balancing chamber does not satisfy any balancing function, but rather enables a push/pull operation.

The device in accordance with the invention can generally be configured to carry out a hemodialysis treatment or a hemodiafiltration treatment, wherein the concept in accordance with the invention is in particular suitable for an application as part of a hemodialysis treatment due to the achievable pressure differences. It enables an increased substituate feed via the dialyzer membrane and an increased removal of uremic toxins without any complex provision of a substituate line and a substituate preparation as is required in hemodiafiltration. A particularly high removal of uremic toxins is thereby achieved with a small effort.

In a further aspect of the invention, a method of treating a dialysis patient using a dialysis machine in accordance with the invention is proposed, wherein a first treatment period is provided without any push/pull operation and a second treatment period is provided having a push/pull operation. In the first treatment period, a large amount of uremic toxins are still produced so that the efficiency of the push/pull method is not yet optimal. This period can amount to 20 min. to approximately 2.5 h; a time period between 30 min. and 1 h is preferred. A second treatment period follows with a push/pull operation so that a highly efficient treatment is made possible. The treatment quality is thus optimized.

It can therefore be stated in summary that in accordance with the invention a device for enabling a push/pull process management is integrated in the dialysis machine in that a further balancing chamber is arranged close to the dialyzer. Dialyzing solution can then be conveyed to and fro by it. Used dialyzing solution is also pushed back into the dialyzer as part of a push/pull process management at a device in accordance with the invention. A main advantage over known devices is in particular the simple design. No external devices are required that additionally have to be integrated in the machine or in the disposable. Only the arrangement of a further balancing chamber at the machine side is required to implement the idea of the invention.

Figure 2:
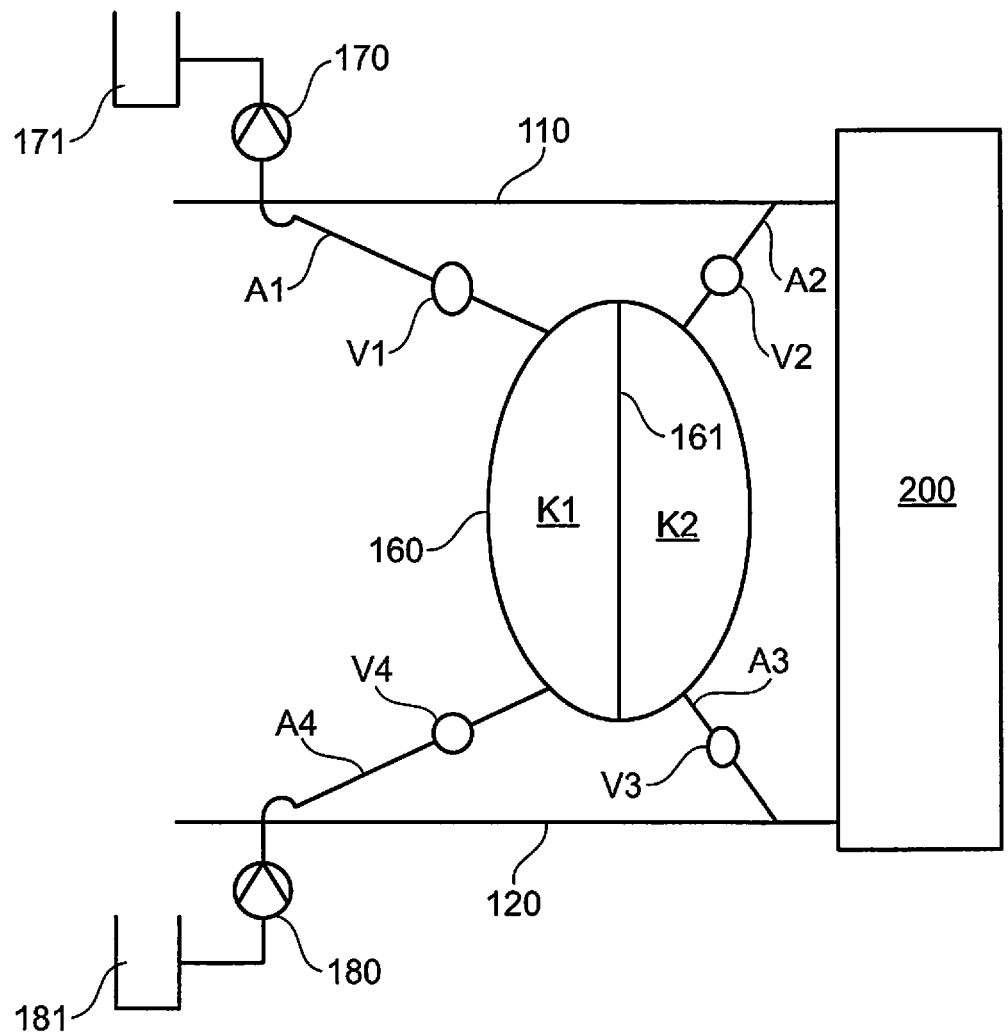
Figure 3A:
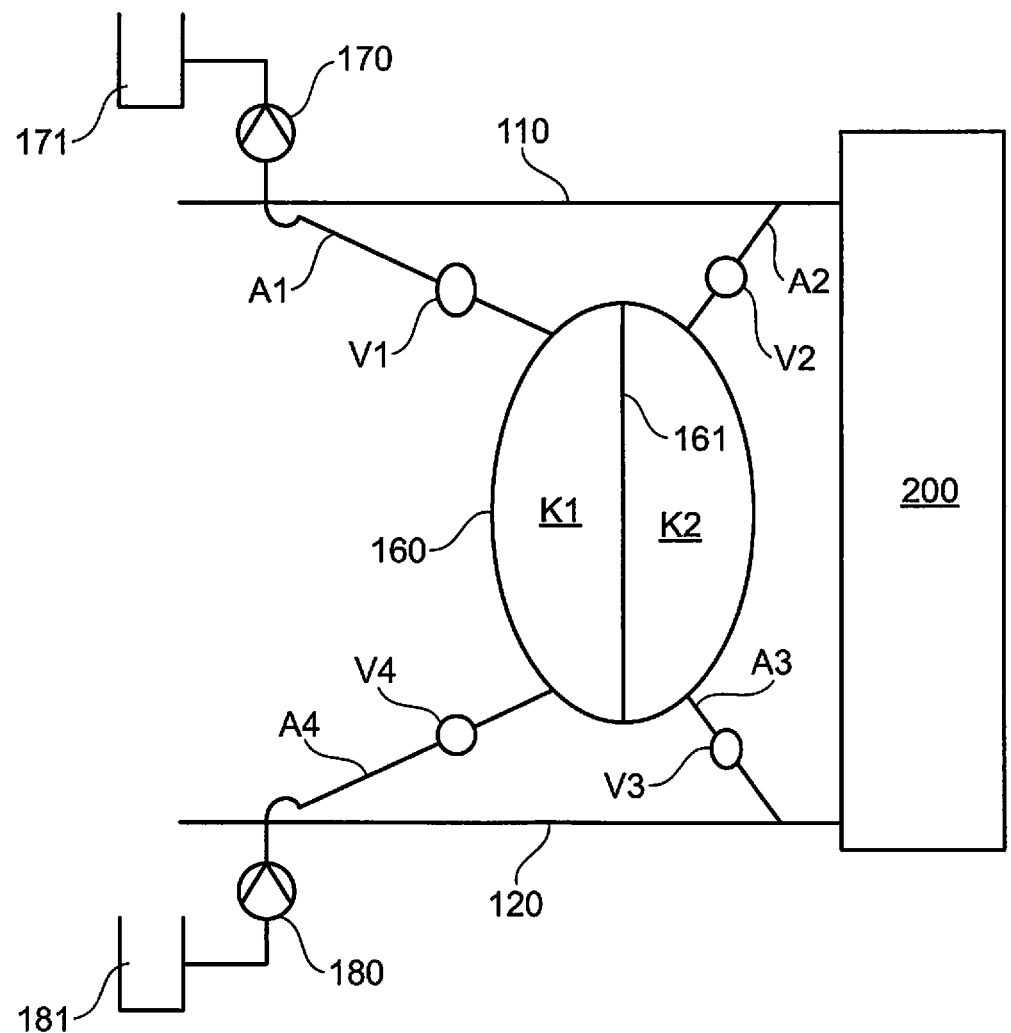
Figure 3B:
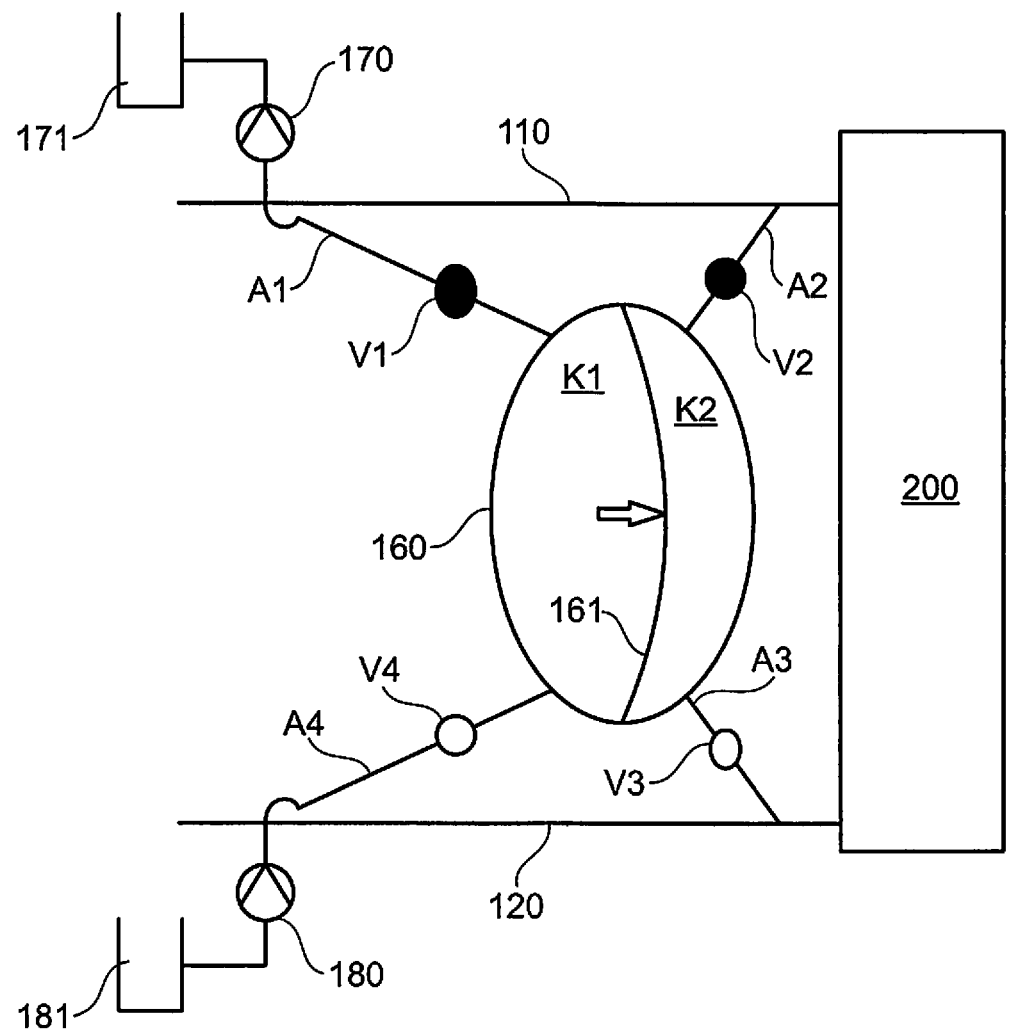
Figure 3C:
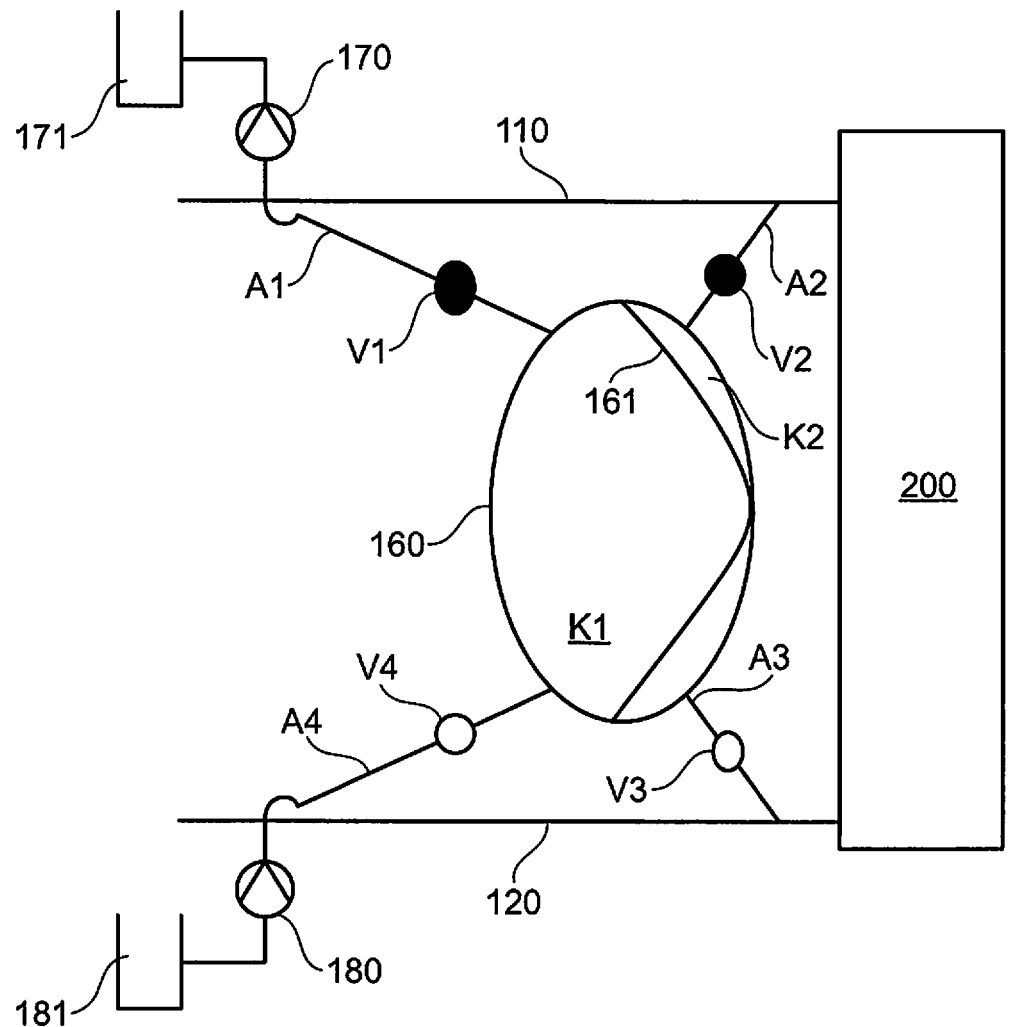
Figure 3D:
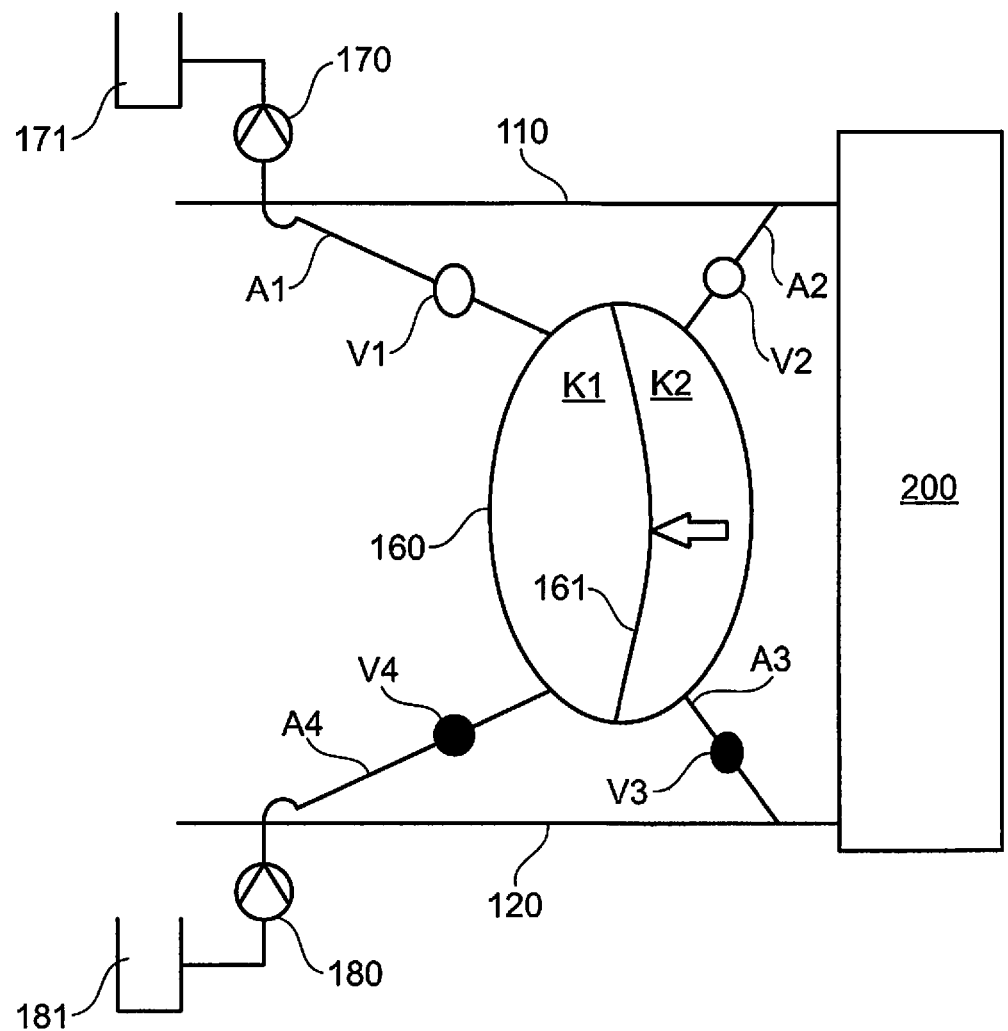
Figure 3E:
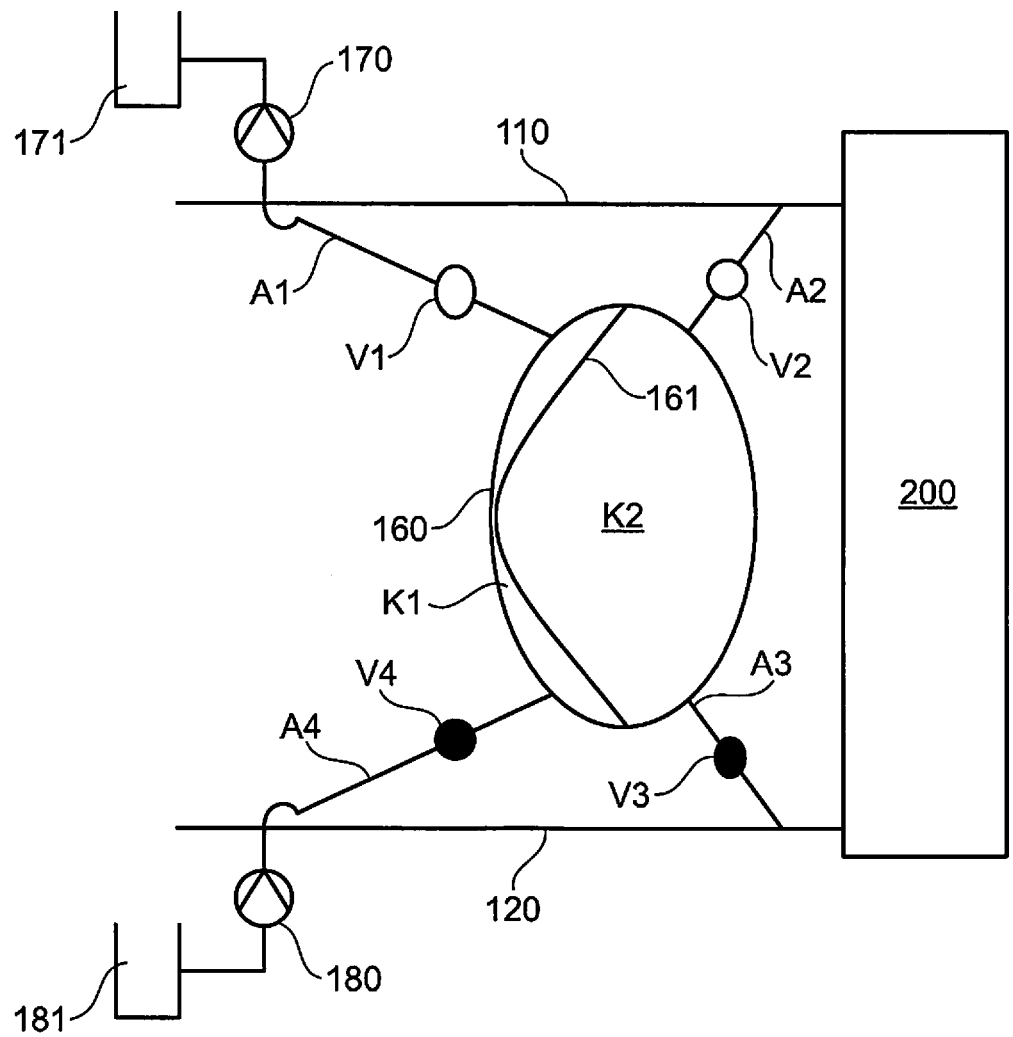
Figure 3F:
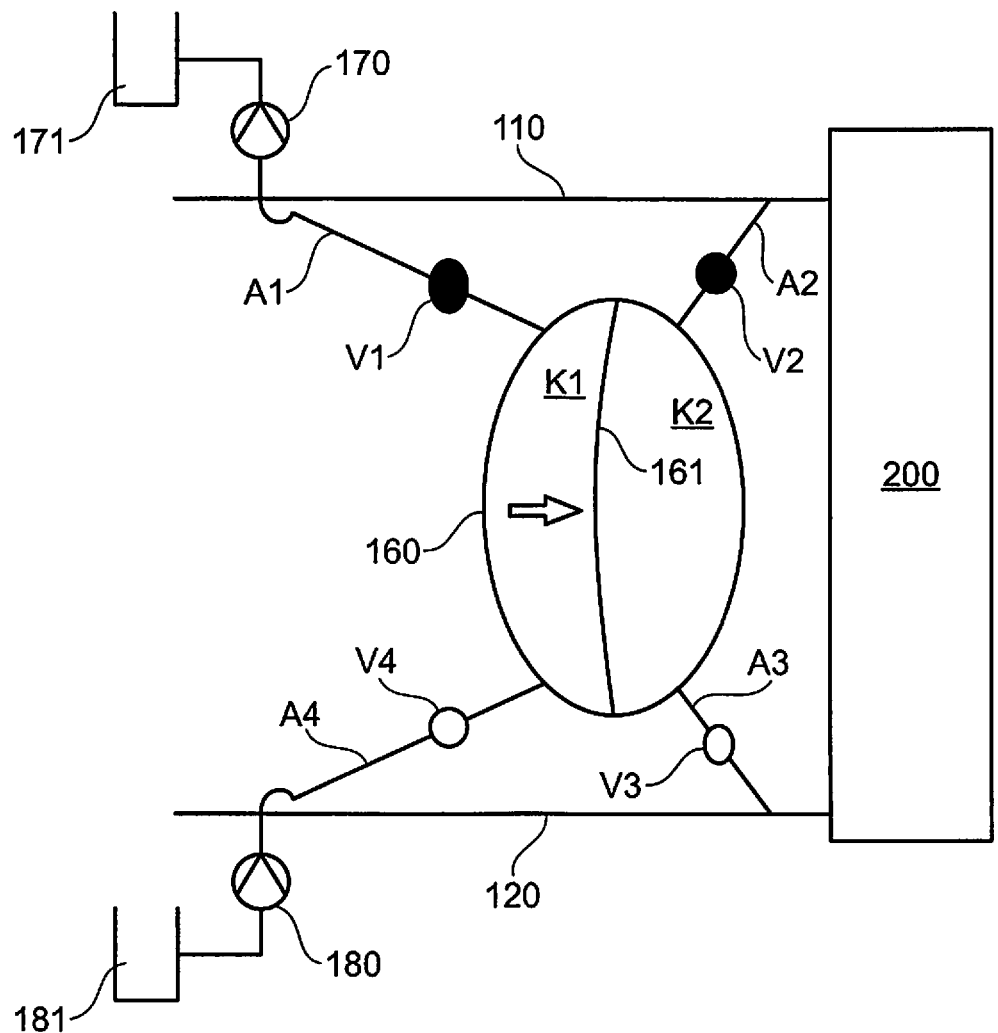
Figure 4:
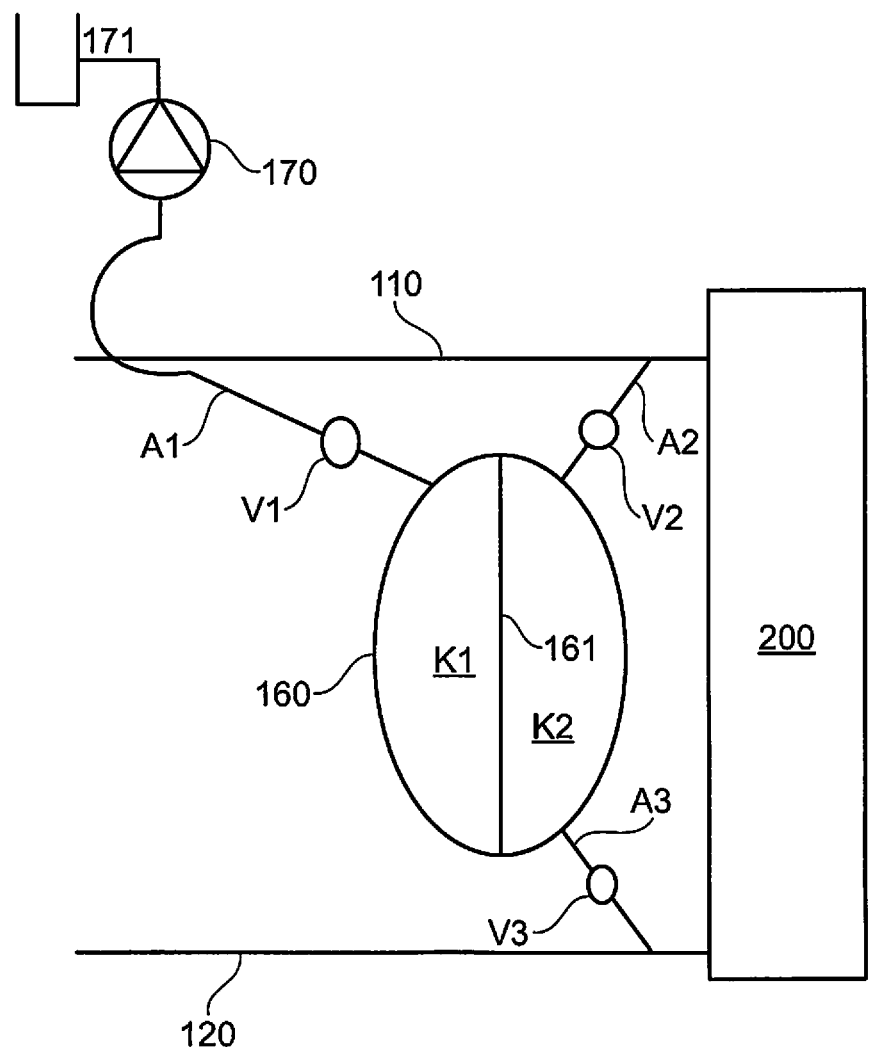

Further details and advantages of the invention result from the following embodiment shown with reference to the Figures. There are shown in the Figures:

FIG. 1: a schematic representation of the fluid system of a dialysis machine in accordance with the invention;

FIG. 2: an enlarged representation of the region around the additional fluid chamber of this system;

FIGS. 3a-3f: representations of the configuration of the region shown in FIG. 2 in different phases of the treatment; and FIG. 4: an enlarged representation of the region around the additional fluid chamber of a further embodiment of a dialysis machine in accordance with the invention.

FIG. 1 shows a schematic representation of the fluid system 100 of a dialysis machine in accordance with the invention that is connected to a dialyzer 200.

The fluid system 100 comprises an inflow line 110 for providing fresh dialyzing solution to the dialyzer 200 and an outflow line 120 for removing used dialyzing solution from the dialyzer. A balancing chamber system 130 is arranged between the lines 110 and 120 and an ultrafiltration line 140 in which an ultrafiltration pump 141 is arranged branches off from the outflow line 120 between the dialyzer 200 and this balancing system 130. An air separator 150 is provided in the region of the branching. The design and function of said components are known do not have to be explained in more detail.

In accordance with the invention, the fluid system comprises an additional balancing chamber 130 that connects a section of the inflow line 110 disposed between the balancing system 130 and the dialyzer 200 to a section of the outflow line 120 disposed between the dialyzer 200 and the branching 120 of the ultrafiltration line 140.

The region around this additional balancing chamber 160 is shown enlarged in FIG. 2.

The fixed volume balancing chamber 160 is divided by an elastic membrane 161 into two chambers K1 and K2 and has four connectors A1, A2, A3, and A4 at which a respective electronically controllable magnetic valve V1, V2, V3, or V4 is arranged to open and close the respective connector, with the magnetic valves V1 and V2 to be considered as optional and also being able to be omitted.

The second connector A2 at least connects the chamber K2 to the inflow line 110 and the third connector A3 connects the chamber K2 to the outflow line 120.

The chamber K1 is connected at the connectors A1 and A4 to respective fluid regulation pumps 170 and 180 that are in turn connected to reservoirs 171 and 181 respectively. The fluid pressure in the chamber K1 can be varied using these pumps 170 and 180 and a push/pull operation can thus ultimately be implemented such as will be explained in even more detail in the following.

The sequence of a push/pull dialysis treatment at a dialysis machine set up in this manner can be understood with reference to FIGS. 3a-3f.

FIG. 3a shows a possible starting position in which all the valves V1-V4 are closed, in which both chambers K1 and K2 are filled with dialyzing solution or fluid, and in which the membrane 161 is in a starting position.

If, as shown in FIG. 3b, the valves V1 and V2 are open, the membrane 161 can be pressed into the chamber K2 with a corresponding pressure buildup by the pump 170 by the pressure in the chamber K1 that is greater in comparison with the pressure in the chamber K2. In this respect, dialyzing solution is displaced from the chamber K2 in the direction of the inflow line 110 and the dialyzate flow is increased. The proportion of the backward filtration in the dialyzer 200 is thus also increased with respect to the starting position in this constellation since the input pressure and thus also the pressure of the dialyzing solution overall is increased at the dialyzer 200.

If the membrane 161 is pressed so far into the chamber K2 that the chamber K1 substantially fills up the total volume of the balancing chamber 161, the pressure at the branching point of the connector A2 falls back to the nominal pressure and the additional dialyzate flow to the dialyzer 200 stops. This is shown in FIG. 3c.

If, as shown in FIG. 3d, the valves V1 and V2 are now closed and instead the valves V3 and V4 are opened, the membrane 161 is pressed back into the chamber K1 with a corresponding suction operation of the pump 180 by the pressure in the chamber K2 that is greater in comparison with the pressure in the chamber K2. In this respect, the chamber K2 is filled with used dialyzing solution while the fluid from the chamber K1 is displaced in the direction of the storage container 181. The proportion of the forward filtration in the dialyzer 200 is thus increased with respect to the starting position in this constellation since the output pressure and thus also the pressure of the dialyzing solution overall is reduced at the dialyzer 200.

If the membrane 161 is pressed so far into the chamber K1 that the chamber K2 substantially fills up the total volume of the balancing chamber 160, the pressure at the branching point of the connector A3 increases back to the nominal pressure and the additional dialyzate flow away from the dialyzer 200 stops. This is shown in FIG. 3e.

If finally the valves V3 and V4 are closed again and instead the valves V1 and V2 are opened again and the pump 170 is operated again, as shown in FIG. 3f, the membrane 161 is pressed back into the chamber K2.

In this respect, the used dialyzing solution is displaced from the chamber K2 in the direction of the inflow line 110 so that the process management in accordance with the invention not only achieves a push/pull effect, but also has the result that a portion of the used dialyzing solution is reused.

This effect in particular shows advantages at the end of a dialysis treatment since there is only a small load of the used dialyzate with uremic toxins at this point in time. It is accordingly preferred that a first treatment period without push/pull operation and a second treatment period with push-push operation are provided.

A variant of the embodiment shown in FIGS. 1-3 is shown in FIG. 4. In this variant, there is no connector A4, no valve V4, no pump 180, and no reservoir 181. The pump 170 is instead configured as a bidirectional pump with which the pressure in the chamber K1 should be increased and decreased. Each opening of the valve V4 described above for the embodiment variant in accordance with FIGS. 1-3 in the operation of the pump 180 is therefore replaced in each case in this embodiment variant with an opening of the valve V1 and a suction operation of the pump 170.

The invention claimed is:

1. A dialysis machine having a fluid system that has an inflow line for providing fresh dialyzing solution to a dialyzer and an outflow line for removing used dialyzing solution from the dialyzer, wherein the fluid system has a balancing system arranged between the inflow and outflow lines to balance the fluid volumes flowing through the lines, and wherein the fluid system has an ultrafiltration line that branches off from the outflow line between the dialyzer and the balancing system and has an ultrafiltration pump to be able to remove a defined volume of used dialyzing solution from the balance, characterized in that an additional balancing chamber is provided that is arranged in a section of the inflow line disposed between the balancing system and the dialyzer or in a section of the outflow line disposed between the dialyzer and the branching of the ultrafiltration line, wherein the additional balancing chamber does not satisfy any balancing function, and wherein the additional balancing chamber enables push/pull operation of the dialysis machine for dialysis treatment.

2. A dialysis machine in accordance with claim 1, characterized in that the additional balancing chamber has a container divided into two chambers, with a connector for connecting the first chamber to the inflow being provided at a first one of the chambers and a connector for connecting the first chamber to the outflow line being provided, and with a valve for opening and closing the respective connector being arranged at both connectors.

3. A dialysis machine in accordance with claim 2, characterized in that at least one connector is provided at the other one of the chambers, that is the second chamber, for connecting the second chamber to a fluid control pump by which the pressure in the second chamber can be raised or lowered.

4. A dialysis machine in accordance with claim 3, characterized in that the fluid control pump is configured such that it can convey fluids in two directions.

5. A dialysis machine in accordance with claim 3, characterized in that two connectors are provided at the second chamber for connecting the second chamber to a respective fluid control pump, with the pressure in the second chamber being able to be raised or lowered by the fluid control pumps.

6. A dialysis machine in accordance with claim 5, characterized in that one of the fluid control pumps is configured such that it can convey fluids into the second chamber and the other one of the fluid control pumps is configured such that it can remove fluids from the second chamber.

7. A dialysis machine in accordance with claim 3, characterized in that the dialysis machine has a control unit that is in signal connection with the valves of the additional balancing chamber and of the fluid control pump or pumps and that is configured to control the valves and pumps such that the pressure of the dialysis solution in the dialyzer is periodically raised and lowered by an alternating filling and emptying of the one chamber of the additional balancing chamber with/of dialyzing solution from the inflow and outflow lines.

8. A dialysis machine in accordance with claim 7, characterized in that the control unit is configured to open the valve connecting the first chamber to the inflow line in a treatment break, to close the valve connecting the first chamber to the outflow line, and to activate the fluid control pump(s) for an input pressure increase of the dialyzing solution at the dialyzer.

9. A dialysis machine in accordance with claim 7, characterized in that the control unit is configured to open the valve connecting the first chamber to the outflow line in a treatment break, to close the valve connecting the first chamber to the inflow line, and to activate the fluid control pump(s) for a pressure reduction in the second chamber to decrease the output pressure of the dialyzing solution at the dialyzer.

10. A dialysis machine in accordance with claim 1, characterized in that the fluid system has an air separator arranged between the dialyzer and the balancing system in the outflow line; and in that the additional balancing chamber is arranged in the section of the inflow line disposed between the balancing system and the dialyzer and a section of the outflow line disposed between the dialyzer and the air separator.

11. A dialysis machine in accordance with claim 1, characterized in that the balancing device is a balancing chamber system having two balancing chambers.

12. A dialysis machine in accordance with claim 1, characterized in that the dialysis machine is a dialysis machine for carrying out a hemodialysis treatment.

13. A method of treating a dialysis patient using a dialysis machine in accordance with claim 1, wherein a first treatment period is provided without a push/pull operation and a second treatment period having a push/pull operation is provided.

14. A dialysis machine in accordance with claim 1, characterized in that the additional balancing chamber has a container of fixed volume divided into two chambers by an elastic membrane, with a connector for connecting the first chamber to the inflow being provided at a first one of the chambers and a connector for connecting the first chamber to the outflow line being provided, and with a valve for opening and closing the respective connector being arranged at both connectors.

15. A dialysis machine in accordance with claim 2, characterized in that at least one connector is provided at the other one of the chambers, that is the second chamber, for connecting the second chamber to a fluid control pump by which the pressure in the second chamber can be raised or lowered, with the connector having a valve for opening and closing the connector.

* * * * *